(12) United States Patent
Mu et al.

(10) Patent No.: US 9,716,239 B2
(45) Date of Patent: Jul. 25, 2017

(54) PHOTOTUNABLE METAL-ORGANIC FRAMEWORK COMPOSITIONS, AND METHODS OF SYNTHESIS THEREOF

(71) Applicant: ARIZONA BOARD OF REGENTS ON BEHALF OF ARIZONA STATE UNIVERSITY, Scottsdale, AZ (US)

(72) Inventors: Bin Mu, Tempe, AZ (US); Bohan Shan, Mesa, AZ (US)

(73) Assignee: ARIZONA BOARD OF REGENTS ON BEHALF OF ARI, Scottsdale, AZ (US)

( * ) Notice: Subject to any disclaimer, the term of this patent is extended or adjusted under 35 U.S.C. 154(b) by 0 days.

(21) Appl. No.: 15/276,377

(22) Filed: Sep. 26, 2016

(65) Prior Publication Data

US 2017/0092879 A1   Mar. 30, 2017

Related U.S. Application Data (60) Provisional application No. 62/232,696, filed on Sep. 25, 2015.

(51) Int. Cl.
*C07F 7/00* (2006.01)
*H01L 51/00* (2006.01)

(52) U.S. Cl.
CPC .......... *H01L 51/0084* (2013.01); *C07F 7/006* (2013.01)

(58) Field of Classification Search
CPC ...................................................... C07F 7/00
USPC ..................................................... 556/51, 55
See application file for complete search history.

(56) References Cited

U.S. PATENT DOCUMENTS 8,653,292 B2   2/2014  Hafizovic et al.
2015/0360201 A1  12/2015  Chen et al.

FOREIGN PATENT DOCUMENTS

WO   WO2014130246 A1   8/2014

OTHER PUBLICATIONS

Gomez-Gualdron, D.A. et al.: Computational design of metal-organic frameworks based on stable Zirconium building units for storage and delivery of methane. Chemistry of Materials, vol. 26, pp. 5632-5639, 2014.*
Yaghi, O. M.; Li, H. Hydrothermal Synthesis of a Metal-Organic Framework Containing Large Rectangular Channels. Am. Chem. Soc. 1995, 117, 10401-10402.
Zhou, H.-C.; Long, J. R.; Yaghi, O. M. Introduction to Metal-Organic Frameworks. Chem. Rev. 2012, 673-674.
Hu, Z.; Deibert, B. J.; Li, J. Luminescent metal-organic frameworks for chemical sensing and explosive detection. Chem. Soc. Rev. 2014, 43, 5815-5840.
Kreno, L. E.; Leong, K.; Farha, O. K.; Allendorf, M.; Van Duyne, R. P.; Hupp, J. T. Metal-organic framework materials as chemical sensors. Chem. Rev. 2012, 112, 1105-1125.
Liu, Y.; Wang, Z. U.; Zhou, H.-C. Recent advances in carbon dioxide capture with metal-organic frameworks. Greenh. Gases Sci. Technol. 2012, 2, 239-259.
Li, J. R.; Sculley, J.; Zhou, H.-C. Metal-organic frameworks for separations. Chem. Rev. 2012, 112, 869-932.
Horcajada, P.; Gref, R.; Baati, T.; Allan, P. K.; Maurin, G.; Couvreur, P.; Férey, G.; Morris, R. E.; Serre, C. Metal-Organic Frameworks in Biomedicine. Chem. Rev. 2012, 112, 1232-1268.
Zhang, M.; Bosch, M.; Gentle III, T.; Zhou, H.-C. Rational design of metal-organic frameworks with anticipated porosities and functionalities. CrystEngComm. 2014, 16, 4069-4083.
Du, M.; Li, C.-P.; Liu, C.-S.; Fang, S.-M. Design and construction of coordination polymers with mixed-ligand synthetic strategy. Coord. Chem. Rev. 2013, 257, 1282-1305.
Farha, O. K.; Hupp, J. T. Rational Design, Synthesis, Purification, and Activation of Metal-Organic Framework Materials. Acc. Chem. Res. 2010, 43, 1166-1175.
He, Y.; Zhou, W.; Qian, G.; Chen, B. Methane storage in metal-organic frameworks. Chem. Soc. Rev. 2014, 43, 5657-5678.
Flage-Larsen, E.; Røyset, A.; Cavka, J. H.; Thorshaug, K. Band Gap Modulations in UiO Metal-Organic Frameworks. J. Phys. Chem. C. 2013, 117, 20610-20616.
Wang, C.-C.; Li, J.-R.; LV, X.-L.; Zhang, Y.-Q.; Guo, G. Photocatalytic organic pollutants degradation in metal-organic frameworks. Energy Environ. Sci. 2014, 00, 1-37.
Yang, L. M.; Fang, G. Y.; Ma, J.; Ganz, E.; Han, S. S. Band Gap Engineering of Paradigm MOF-5. Cryst. Growth Des. 2014, 14, 2532-2541.
Hendon, C. H.; Tiana, D.; Fontecave, M.; Sanchez, C.; D'Arras, L.; Sassoye, C.; Rozes, L.; Mellot-Draznieks, C.; Walsh, A. J. Engineering the Optical Response of the Titanium-MIL-125 Metal-Organic Framework through Ligand Functionalization. Am. Chem. Soc. 2013, 135, 10942-10945.
Gascon, J.; Hernández-Alonso, M. D.; Almeida, A. R.; Van Klink, G. P. M.; Kapteijn, F.; Mul, G. Isoreticular MOFs as Efficient Photocatalysts with Tunable Band Gap: An Operando FTIR Study of the Photoinduced Oxidation of Propylene. ChemSusChem. 2008, 1, 981-983.
Lin, C.-K.; Zhao, D.; Gao, W.-Y.; Yang, Z.; Ye, J.; Xu, T.; Ge, Q.; Ma, S.; Liu, D.-J. Tunability of Band Gaps in Metal-Organic Frameworks. Inorg. Chem. 2012, 51, 9039-9044.

(Continued)

*Primary Examiner* — Charanjit Aulakh
(74) *Attorney, Agent, or Firm* — Greenberg Traurig, LLP (57) ABSTRACT

Some embodiments include a method of preparing a phototuned metal-organic framework by forming a first solution by dissolving $ZrOCl_2 \cdot 8H_2O$ in dimethylformamide (DMF) and formic acid, mixing and dissolving 1,4-phenylenediacrylic acid in a second solution of dimethylformamide (DMF) and trimethylamine, and at least partially mixing the first and second solutions to form a mixture. The method further includes sealing the mixture in an autoclave and heating the mixture to above ambient temperature for a specified period of time to prepare ZrPDA metal-organic framework, and extracting the ZrPDA metal-organic framework and at least partially reacting to a specified degree at least some of ZrPDA metal-organic framework through [2+2] cycloaddition reactions. The specified degree can be tunable based at least in part on at least one of the intensity of UV radiation, the exposure time, and the UV wavelength.

20 Claims, 12 Drawing Sheets

(56) References Cited

OTHER PUBLICATIONS

Stuart, M. A C.; Huck, W. T. S.; Genzer, J.; Müller, M.; Ober, C.; Stamm, M.; Sukhorukov, G. B.; Szleifer, I.; Tsukruk, V. V; Urban, M.; Winnik, F.; Zauscher, S.; Luzinov, I.; Minko, S. Emerging applications of stimuli-responsive polymer materials. Nat. Mater. 2010, 9, 101-113.

Mignon, A.; Graulus, G.-J.; Snoeck, D.; Martins, J.; De Belie, N.; Dubruel, P.; Van Vlierberghe, S. pH-sensitive superabsorbent polymers: a potential candidate material for self-healing concrete. J. Mater. Sci. 2014, 50, 970-979.

Guan, Y.; Zhao, H.-B.; Yu, L.-X.; Chen, S.-C.; Wang, Y.-Z. Multi-stimuli sensitive supramolecular hydrogel formed by host-guest interaction between PNIPAM-Azo and cyclodextrin dimers. RSC Adv. 2014, 4, 4955-4959.

Amiri, S.; Duroux, L.; Nielsen, T. T.; Larsen, K. L. Preparation and Characterization of a Temperature-Sensitive Nonwoven Poly(propylene) with Increased Affinity for Guest Molecules J. Appl. Polym. Sci. 2014, 131, 40497-40504.

Davis, D. A; Hamilton, A.; Yang, J.; Cremar, L. D.; Van Gough, D.; Potisek, S. L.; Ong, M. T.; Braun, P. V; Martínez, T. J.; White, S. R.; Moore, J. S.; Sottos, N. R. Force-induced activation of covalent bonds in mechanoresponsive polymeric materials. Nature. 2009, 459, 68-72.

Cavka, J. H.; Jakobsen, S.; Olsbye, U.; Guillou, N.; Lamberti, C.; Bordiga, S.; Lillerud, K. P. A New Zirconium Inorganic Building Brick Forming Metal Organic Frameworks with Exceptional Stability. J. Am. Chem. Soc. 2008, 130, 13850-13851.

Wu, H.; Yildirim, T.; Zhou, W. Exceptional Mechanical Stability of Highly Porous Zirconium Metal-Organic Framework UiO-66 and Its Important Implications. J. Phys. Chem. Lett. 2013, 4, 925-930.

Chae, B.; Lee, S. W.; Ree, M.; Jung, Y. M.; Kim, S. B. Photoreaction and Molecular Reorientation in a Nanoscaled Film of Poly(methyl 4-(methacryloyloxy)cinnamate) Studied by Two-Dimensional FTIR and UV Correlation Spectroscopy. Langmuir. 2003, 19, 687-695.

Cho, S.-Y.; Kim, J.-G.; Chung, C.-M. A fluorescent crack sensor based on cyclobutane-containing crosslinked of tricinnamates. Sensors Actuators, B Chem. 2008, 134, 822-825. polymers.

Zou, J.; Liu, Y.; Shan, B.; Chattopadhyay, A.; Dai, L. L. Early damage detection in epoxy matrix using cyclobutane-based polymers. Smart Mater. Struct. 2014, 23, 095038.

Chae, B.; Lee, S. W.; Jung, Y. M.; Ree, M.; Kim, S.-B. Two-Dimensional Correlation Analysis Study of the Photo-Induced Molecular Reorientations of Photosensitive Polyester Film Containing 1,4-Phenylenediacryloyl Units in the Backbone. Appl. Spectrosc. 2008, 62, 497-502.

Coleman, M. M.; Hu, Y. I. N.; Sobkowiak, M.; Painter, P. C. Infrared Characterization of Poly(vinyl cinnamate) and Its Blends with Poly(4-vinyl phenol) before and after UV Exposure. J. Polym. Sci. Part B Polym. Phys. 1997, 36, 1579-1590.

Tauc, J. Optical Properties and Electronic Structure of Amorphous Ge and Si. Mater. Res. Bull. 1968, 3, 37-46.

Valenzano, L.; Civalleri, B.; Chavan, S.; Bordiga, S.; Nilsen, M. H.; Jakobsen, S.; Lillerud, K. P.; Lamberti, C. Disclosing the Complex Structure of UiO-66 Metal Organic Framework: A Synergic Combination of Experiment and Theory. Chem. Mater. 2011, 23, 1700-1718.

Wang, C.; Volotskova, O.; Lu, K.; Ahmad, M.; Sun, C.; Xing, L.; Lin, W. Synergistic Assembly of Heavy Metal Clusters and Luminescent Organic Bridging Ligands in Metal-Organic Frameworks for Highly Efficient X-ray Scintillation. J. Am. Chem. Soc. 2014, 136, 6171-6174.

Kawatsuki, N.; Matsuyoshi, K.; Hayashi, M.; Takatsuka, H.; Yamamoto, T. Photoreaction of Photo-cross-linkable Methacrylate Polymer Films Comprising 2-Cinnamoyloxyethoxybiphenyl Side Group by Linearly Polarized Ultraviolet Light and Liquid Crystal Alignment on the Resultant Films. Chem. Mater. 2000, 12, 1549-1555.

Flage-Larsen, E.; Thorshaug, K. Linker Conformation Effects on the Band Gap in Metal-Organic Frameworks. Inorg. Chem. 2014, 53, 2569-2572.

Decoste, J. B.; Peterson, G. W.; Jasuja, H.; Glover, T. G.; Huang, Y.; Walton, K. S. Stability and degradation mechanisms of metal-organic frameworks containing the Zr6O4(OH)4 secondary building unit. J. Mater. Chem. A. 2013, 1, 5642-5650.

Suárez, G.; Sakka, Y.; Suzuki, T.; Uchikoshi, T.; Aglietti, E. F. Texture development in 3 mol% yttria-stabilized tetragonal zirconia. Mater. Res. Bull. 2009, 44, 1802-1805.

Yang, L.-M.; Ganz, E.; Svelle, S.; Tilset, M. Computational exploration of newly synthesized zirconium metal-organic frameworks UiO-66, -67, -68 and analogues. J. Mater. Chem. C. 2014, 2, 7111-7125.

Jasuja, H.; Huang, Y.; Walton, K. S. Adjusting the Stability of Metal-Organic Frameworks under Humid Conditions by Ligand Functionalization. Langmuir. 2012, 28, 16874-16880.

Lu, P.; Wu, Y.; Kang, H.; Wei, H.; Liu, H.; Fang, M. What can pKa and NBO charges of the ligands tell us about the water and thermal stability of metal organic frameworks? J. Mater. Chem. A. 2014, 2, 16250-16267.

Ren, Y.-W.; Liang, J.-X.; Lu, J.-X.; Cai, B.-W.; Shi, D.-B.; Qi, C.-R.; Jiang, H.-F.; Chen, J.; Zheng, D. 1,4-Phenylenediacetate-Based Ln MOFs—Synthesis, Structures, Luminescence, and Catalytic Activity. Eur. J. Inorg. Chem. 2011, 4369-4376.

Guo, Y.; Feng, X.; Han, T.; Wang, S.; Lin, Z.; Dong, Y.; Wang, B. Tuning the Luminescence of Metal-Organic Frameworks for Detection of Energetic Heterocyclic Compounds. J. Am. Chem. Soc. 2014, 136, 15485-15488.

Burtch, N.; Jasuja, H.; Walton, K. S. Water Stability and Adsorption in Metal-Organic Frameworks. Chem. Rev 2014, 114, 10575-10612.

\* cited by examiner

PHOTOTUNABLE METAL-ORGANIC FRAMEWORK COMPOSITIONS, AND METHODS OF SYNTHESIS THEREOF

RELATED APPLICATIONS

This application claims priority to U.S. provisional application Ser. No. 62/232,696, filed on Sep. 25, 2015, the entire contents of which are incorporated herein by reference.

BACKGROUND

Inorganic-organic hybrid materials that include metal-organic frameworks ("MOFs") have attracted intensive attention in recent years. MOFs are known to display the highest reported specific surface area among all porous materials, and can be synthesized from a theoretically infinite combination of metals and linkers. This has made them promising candidates for a diverse range of applications including sensing, separation, and drug delivery.

To establish a thorough structure-property relationship for rational MOF design, numerous studies have explored different functions of various MOFs (e.g., such as for gas storage, sensing, and separation), however few studies have focused on MOF semiconductor materials and properties. Research aimed at exploring the tuning of semiconductor behaviors of MOFs have generally focused on band gap energy variation by changing the different metals and/or linkers involved in the synthesis (see for example Yang, L. M.; Fang, G. Y.; Ma, J.; Ganz, E.; Han, S. S. Cryst. Growth Des. 2014, 14, 2532-2541, and Hendon, C. H.; Tiana, D.; Fontecave, M.; Sanchez, C.; D'arras, L.; Sassoye, C.; Rozes, L.; Mellot-Draznieks, C.; Walsh, A. J. Am. Chem. Soc. 2013, 135, 10942-10945). Some structure to property relationship studies have shown that varying organic linkers can significantly impact the bulk optical band gap energy (see for example Gascon, J.; Hernández-Alonso, M. D.; Almeida, A. R.; van Klink, G. P. M.; Kapteijn, F.; Mul, G. ChemSusChem 2008, 1, 981-983).

Numerous studies have been performed focusing on varying the ligand to change optical band gap energy, however these attempts were mostly made before synthesis (see for example Flage-Larsen, E.; Royset, A.; Cavka, J. H.; Thorshaug, K. J. Phys. Chem. C 2013, 117, 20610-20616, and Lin, C.-K.; Zhao, D.; Gao, W.-Y.; Yang, Z.; Ye, J.; Xu, T.; Ge, Q.; Ma, S.; Liu, D.-J. Inorg. Chem. 2012, 51, 9039-9044). Furthermore, the modification of the optical band gap energy through internal in-situ reactions using controllable external stimuli has not been widely explored.

SUMMARY OF THE INVENTION

Some embodiments include a metal-organic framework material preparation method comprising, 1) in a first step, forming a first solution by dissolving $ZrOCl_2 \cdot 8H_2O$ in dimethylformamide (DMF) and formic acid, and 2) in a second step, mixing and dissolving 1,4-phenylenediacrylic acid in a second solution of dimethylformamide (DMF) and trimethylamine; 3) in a third step, at least partially mixing the first and second solutions to form a mixture; and 4) in a fourth step, sealing the mixture in an autoclave and heating the mixture above ambient for a specified period of time to prepare ZrPDA metal-organic framework.

In some embodiments, the second step occurs after completion of the first step. In some further embodiments, the second step is performed at least partially concurrently with the first step. In some embodiments, during the fourth step, the mixture is heated to a temperature between ambient temperature and 200° C.

In some embodiments, during the fourth step, the mixture is heated to about 120° C. In some embodiments, the specified period of time is between about 24 hours and 1 week. In some embodiments, the specified period of time is about 24 hours. In some further embodiments, in a fifth step, the ZrPDA metal-organic framework is washed with dimethylformamide (DMF). In further embodiments, the ZrPDA metal-organic framework is washed with dimethylformamide (DMF) at least twice. In some other embodiments, the ZrPDA metal-organic framework is washed with dimethylformamide (DMF) three times per day for three days. Some embodiments include a sixth step where the ZrPDA metal-organic framework is soaked in acetone and solvent exchanged for a specified exchange period. In some embodiments, the solvent exchange occurs at least twice. In some embodiments, the exchange period is three days, and the acetone is changed three times per day. In some embodiments, the ZrPDA metal-organic framework is heated to about 100° C. in a vacuum oven.

Some embodiments include a method of preparing a phototuned metal-organic framework comprising: 1) in a first step, forming a first solution by dissolving ZrOCl2.8H2O in dimethylformamide (DMF) and formic acid, and 2) in a second step, mixing and dissolving 1,4-phenylenediacrylic acid in a second solution of dimethylformamide (DMF) and trimethylamine; and 3) in a third step, at least partially mixing the first and second solutions to form a mixture; and 4) in a fourth step, sealing the mixture in an autoclave and heating the mixture to above ambient temperature for a specified period of time to prepare ZrPDA metal-organic framework; and 5). in a fifth step, extracting the ZrPDA metal-organic framework and at least partially reacting to a specified degree at least some of ZrPDA metal-organic framework through [2+2] cycloaddition reactions, wherein the specified degree is tunable based at least in part on at least one of the intensity of UV radiation, the exposure time, and the UV wavelength.

In some embodiments, the specified time is between 24 hours and 1 week. In some further embodiments, in the fourth step, the mixture is heated to between 50° C. and 200° C. In some embodiments, the UV wavelength is about 302 nm. In some further embodiments, the exposure time is greater than zero and less than 60 minutes. In some further embodiments, the exposure time is between about 60 minutes and 2 hours.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Some embodiments of the invention include the use functional molecules that can respond to various external stimulus (e.g., including, but not limited to pH changes, light irradiation, temperature change, pressure change, etc.,) By introducing smart molecules into frameworks, one or more properties of the material can be influenced or changed using one or more external stimuli.

Embodiments of the invention described herein include Zirconium-based MOFs synthesized with a photo-active linker molecule that is able to produce a microporous material with a specific surface area higher than 1000 $m^3/g$. Further, the optical band gap energy can be varied by UV irradiation in solid state. In contrast to the low stability of conventional metal-organic frameworks, Zirconium-based MOFs synthesize using the methods described herein can be highly moisture or water stable. For example, the crystal structure can remain substantially stable under water for at least 672 hours. The tunable optical band gap energy, high specific surface area, and high hydrostability of these materials provide use in a wide range of applications, including, but not limited to photocatalysis, semiconductors, and energy harvesting.

Figure 1A:
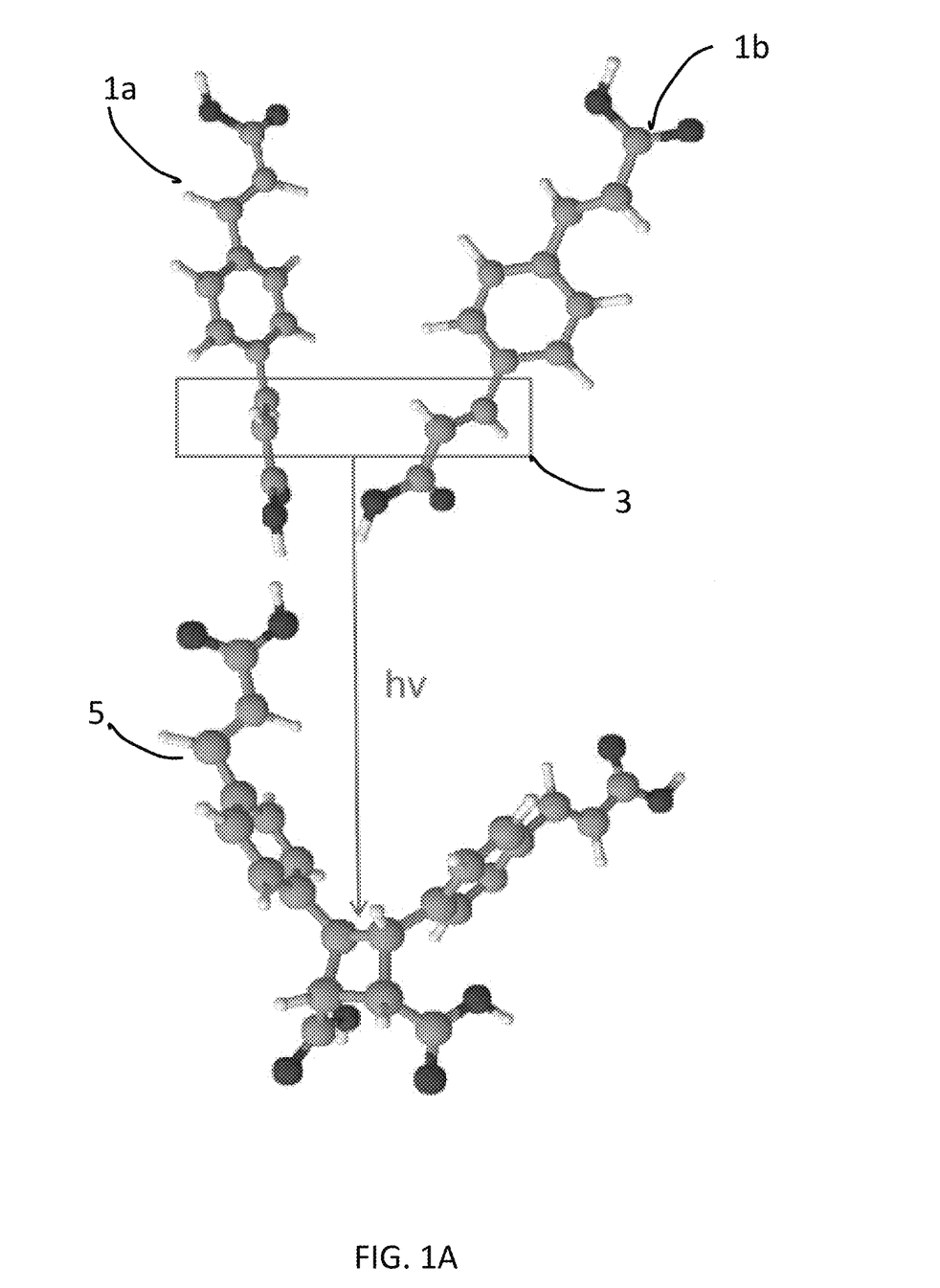
FIG. 1A illustrates a ZrPDA formation reaction in accordance with some embodiments of the invention.

Embodiments of the invention described herein include Zirconium-based MOFs synthesized with 1,4-phenylenediacrylic acid ($H_2PDA$). 1,4-phenylenediacrylic acid ($H_2PDA$) is just one of a number of compounds containing cinnamoyl moieties that undergo a [2+2] cycloaddition reaction under UV irradiation. Using the methods described therein, Zirconium-based MOFs that are hydro-stable and with in-situ photo-tunable properties can be synthesized. Conventional commercially available materials were used as received without any further purification to produce Zirconium-1,4-phenylenediacrylic acid (ZrPDA) that can undergo cycloaddition. For example, referring to FIG. 1A, illustrating a ZrPDA, some embodiments include the synthesis of Zirconium-based MOFs (shown as 1a, 1b), that can undergo photodimerization using UV irradiation to form a [2+2] cycloaddition product 5 through a [2+2] cycloaddition of cinnamoyl groups (shown as 3).

In some embodiments, ZrPDA precursor materials can include Zirconium oxychloride octahydrate ($ZrOCl_2.8H_2O$), Formic Acid, and 1,4-Phenylenediacrylic Acid ($H_2PDA$) from Sigma Aldrich. N,N-Dimethylformamide (DMF) and acetone can be sourced from Fisher Scientific, and Triethylamine (TEA) can be sourced commercially from Alfa Aesar. Some embodiments include methods of synthesis of ZrPDA compounds including a first step, where $ZrOCl_2.8H_2O$ (about 0.161 g, 0.5 mmol) can be dissolved in a mixture of about 15 mL of DMF and about 2.3 mL of formic acid. In a second sequential or concurrent step, 1,4-phenylenediacrylic acid (about 0.109 g, 0.5 mmol) can be mixed and dissolved in a solution containing about 15 mL of DMF and about 0.15 mL of trimethylamine. In a third step, the two solutions ($ZrOCl_2.8H_2O$/DMF/formic acid and 1,4-phenylenediacrylic acid/DMF/trimethylamine) can be mixed and sealed in a Teflon lined stainless steel autoclave. In some embodiments, the autoclave can be heated to about 120° C. and held for about 24 hours. Subsequently, the synthesized samples can be washed with DMF three times a day for three days. In some embodiments, samples can be soaked in acetone for solvent exchange, and the solvent changed three times a day for three days. Further, in some embodiments, the sample can be heated to about 100° C. in vacuum oven and maintained for 24 hours. In some other embodiments of the invention, other metals can be used in place of or in addition to Zirconium. For example, in some embodiments, Titanium and/or Hafnium can be used. In some further embodiments, other transition metals and/or group 13 and/or group 14 metals can be used including, but not limited to, Zinc, Copper, Nickel, Cobalt, Iron, Manganese, Chromium, Vanadium, Cadmium, Aluminum, Gallium, Indium, Tin, Scandium, Yttrium, and/or any lanthanide series metal.

Figure 1B:
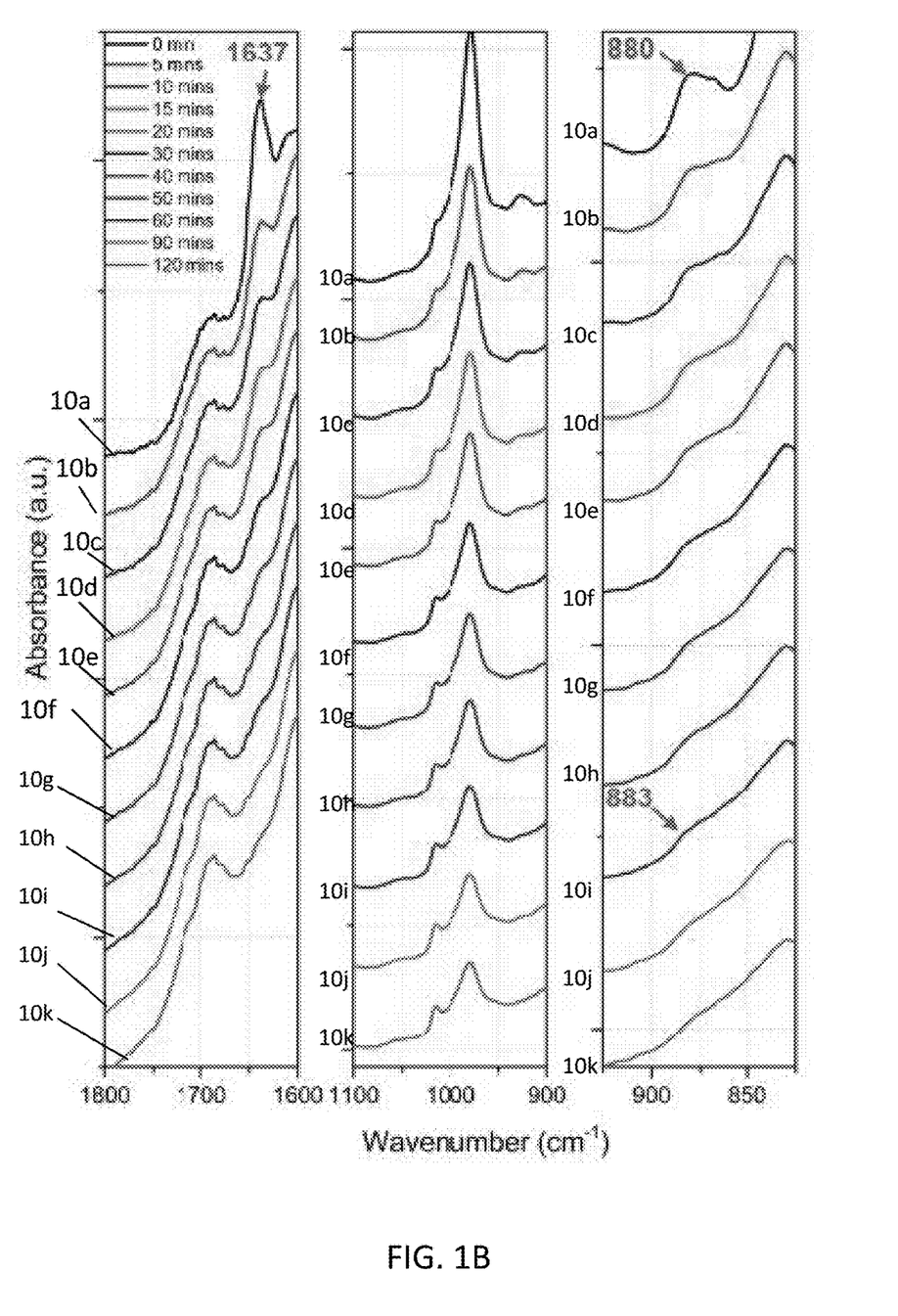
FIG. 1B illustrates an FTIR spectra of ZrPDA with varying UV exposure times in accordance with some embodiments of the invention.

In some further embodiments, the ZrPDA synthesized using the methods described above can be exposed to UV irradiation (e.g., with a wavelength of about 302 nm and with varying exposure time). Using a AUV-Vis spectrometer, FT-IR spectrometer, and spectrofluorometer, the change of optical band gap energy of ZrPDA can be monitored. In some embodiments, the optical band gap energy of ZrPDA can be lowered after being exposed under UV irradiation as described. Further, FTIR, XRD, and photoluminescence of the ZrPDA following UV exposure causing [2+2] cycloaddition can be used to characterize the development of photodimerized ZrPDA (shown as 5 in FIG. 1A). For example, FIG. 1B illustrates an FTIR spectra of various ZrPDA materials with varying UV exposure times in accordance with some embodiments of the invention. The exposure times include no exposure (shown as curve 10a), a 5 minute UV exposure time (shown as curve 10b), a 10 minute UV exposure (shown as curve 10c), a 15 minute UV exposure (shown as curve 10d), a 20 minute UV exposure (shown as curve 10e), a 30 minute UV exposure (shown as curve 10f), a 40 minute UV exposure (shown as curve 10g), a 50 minute UV exposure (shown as curve 10h), a 60 minute UV exposure (shown as curve 10i), a 90 minute UV exposure (shown as curve 10j), and a 120 minute UV exposure (shown as curve 10k).

Figure 1C:
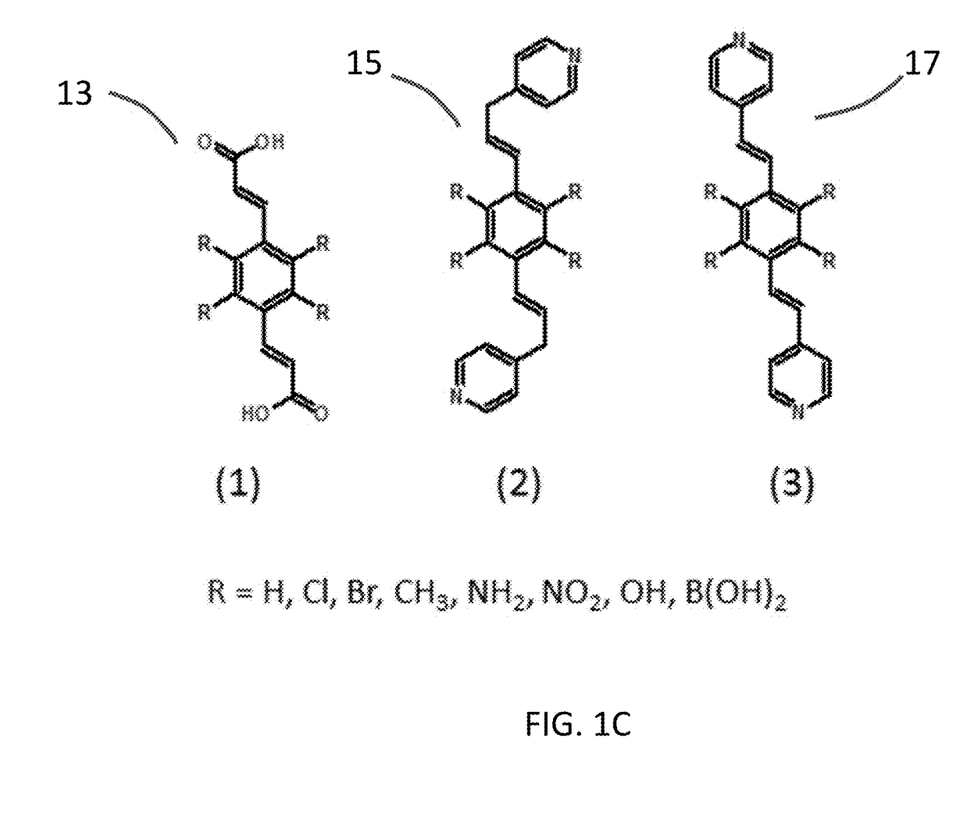
FIG. 1C shows alternative linker structures to 1,4-phenylenediacrylic acid in accordance with some other embodiments of the invention.

FIG. 1C shows various linker structures to 1,4-phenylenediacrylic acid in accordance with some embodiments of the invention. For example, in some embodiments, the UV active linker molecule can comprise linker 1 (shown as structure 13) as shown with various substitutions including one or more of those shown in Table 1 below:

TABLE 1 linkers based on Ligand 1 of FIG. 1C

| R | Name |
|---|---|
| H | 1,4-Phenylenediacrylic acid |
| Cl | (2E,2'E)-3,3'-(perchloro-1,4-phenylene)diacrylic acid |
| Br | (2E,2'E)-3,3'-(perbromo-1,4-phenylene)diacrylic acid |
| $CH_3$ | (2E,2'E)-3,3'-(2,3,5,6-tetramethyl-1,4-phenylene)diacrylic acid |
| $NH_2$ | (2E,2'E)-3,3'-(2,3,5,6-tetraamino-1,4-phenylene)diacrylic acid |
| $NO_2$ | (2E,2'E)-3,3'-(2,3,5,6-tetranitro-1,4-phenylene)diacrylic acid |
| OH | (2E,2'E)-3,3'-(2,3,5,6-tetrahydroxy-1,4-phenylene)diacrylic acid |
| $B(OH)_2$ | (2E,2'E)-3,3'-(2,3,5,6-tetraborono-1,4-phenylene)diacrylic acid |

In some further embodiments, the UV active linker molecule can comprise linker 2 (shown as structure 15) as shown with various substitutions including one or more of those shown in Table 2 below:

TABLE 2

Alternative linkers based on Ligand 2 of FIG. 1C

| R | Name |
|---|---|
| H | 1,4-bis(3-(4-pyridinyl)propenyl)benzene |
| Cl | 4,4'-((2E,2'E)-(perchloro-1,4-phenylene)bis(prop-2-ene-3,1-diyl))dipyridine |
| Br | 4,4'-((2E,2'E)-(perbromo-1,4-phenylene)bis(prop-2-ene-3,1-diyl))dipyridine |

TABLE 2-continued

Alternative linkers based on Ligand 2 of FIG. 1C

| R | Name |
|---|---|
| $CH_3$ | 4,4'-((2E,2'E)-(2,3,5,6-tetramethyl-1,4-phenylene)bis(prop-2-ene-3,1-diyl))dipyridine |
| $NH_2$ | 3,6-bis((E)-3-(pyridin-4-yl)prop-1-en-1-yl)benzene-1,2,4,5-tetraamine |
| $NO_2$ | 4,4'-((2E,2'E)-(pernitro-1,4-phenylene)bis(prop-2-ene-3,1-diyl))dipyridine |
| OH | 3,6-bis((E)-3-(pyridin-4-yl)prop-1-en-1-yl)benzene-1,2,4,5-tetraol |
| $B(OH)_2$ | 3,6-bis((E)-3-(pyridin-4-yl)prop-1-en-1-yl)benzene-1,2,4,5-tetrayl)tetraboronic acid |

In some other embodiments, the UV active linker molecule can comprise linker 3 (shown as structure 17) as shown with various substitutions including one or more of those shown in Table 3:

linkers based on Ligand 3 of FIG. 1C

| R | Name |
|---|---|
| H | 1,4-bis((E)-2-(pyridinyl-4-yl)vinyl)benzene |
| Cl | 4,4'-((1E,1'E)-(perchloro-1,4-phenylene)bis(ethene-2,1-diyl))dipyridine |
| Br | 4,4'-((1E,1'E)-(perbromo-1,4-phenylene)bis(ethene-2,1-diyl))dipyridine |
| $CH_3$ | 4,4'-((1E,1'E)-(2,3,5,6-tetramethyl-1,4-phenylene)bis ethene-2,1-diyl))dipyridine |
| $NH_2$ | 3,6-bis((E)-2-(pyridin-4-yl)vinyl)benzene-1,2,4,5-tetraamine |
| $NO_2$ | 4,4'-((1E,1'E)-(pernitro-1,4-phenylene)bis(ethene-2,1-diyl))dipyridine |
| OH | 3,6-bis((E)-2-(pyridin-4-yl)vinyl)benzene-1,2,4,5-tetraol |
| $B(OH)_2$ | (3,6-bis((E)-2-(pyridin-4-yl)vinyl)benzene-1,2,4,5-tetrayl)tetraboronic acid |

Figure 2A:
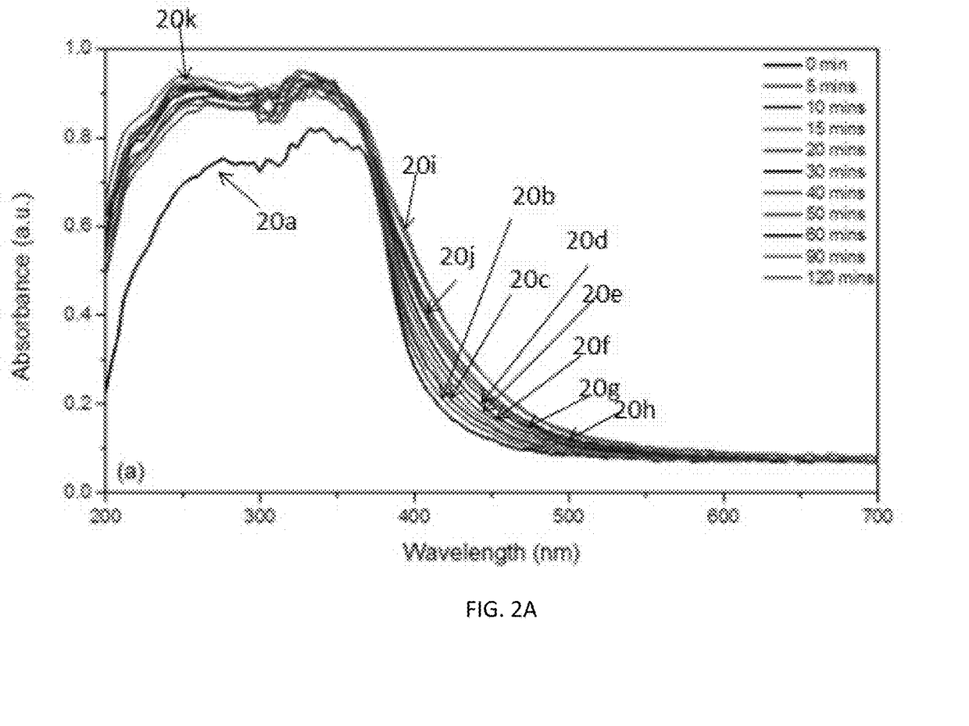
FIG. 2A shows UV-VIS spectra of activated ZrPDA with varying UV exposure time in accordance with some embodiments of the invention.

Further, FIG. 2A shows UV-VIS spectra of activated ZrPDA with varying UV exposure time in accordance with some embodiments of the invention. The exposure times include no exposure (shown as curve 20a), 5 minute exposure (shown as curve 20b), 10 minute exposure (shown as curve 20c), 15 minute exposure (shown as curve 20d), 20 minute exposure (shown as curve 20e), 30 minute exposure (shown as curve 20f), 40 minute exposure (shown as curve 20g), 50 minute exposure (shown as curve 20h), 60 minute exposure (shown as curve 20i), 90 minute exposure (shown as curve 20j), and 120 minute exposure (shown as curve 20k).

Figure 2B:
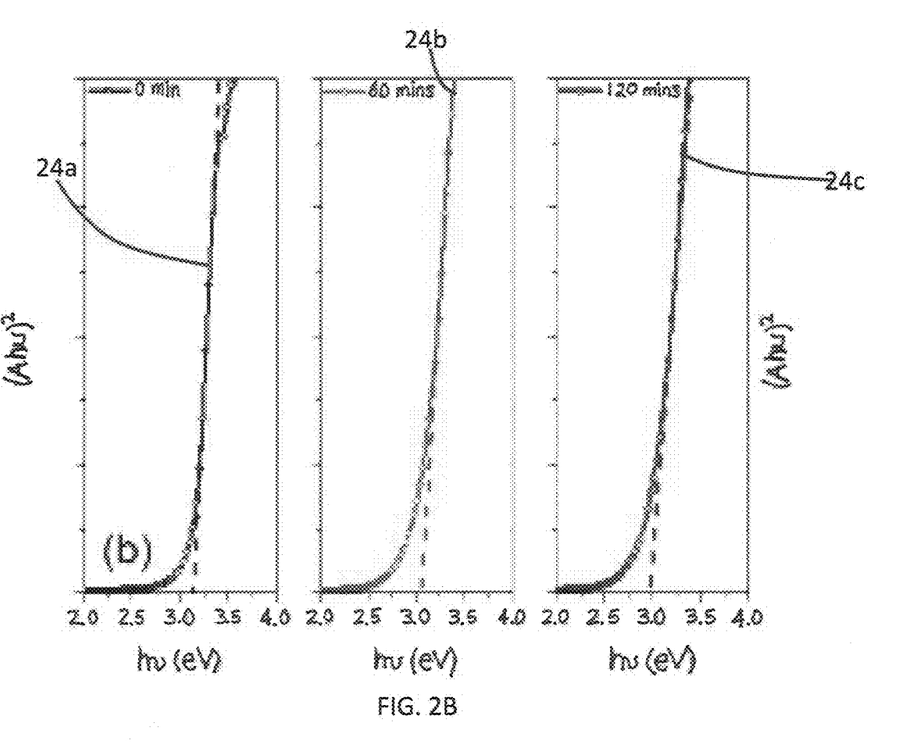
FIG. 2B shows the optical band gap energies of activated ZrPDA with 0 minute, 60 minutes, and 120 minutes of UV exposure in accordance with some embodiments of the invention.
Figure 2C:
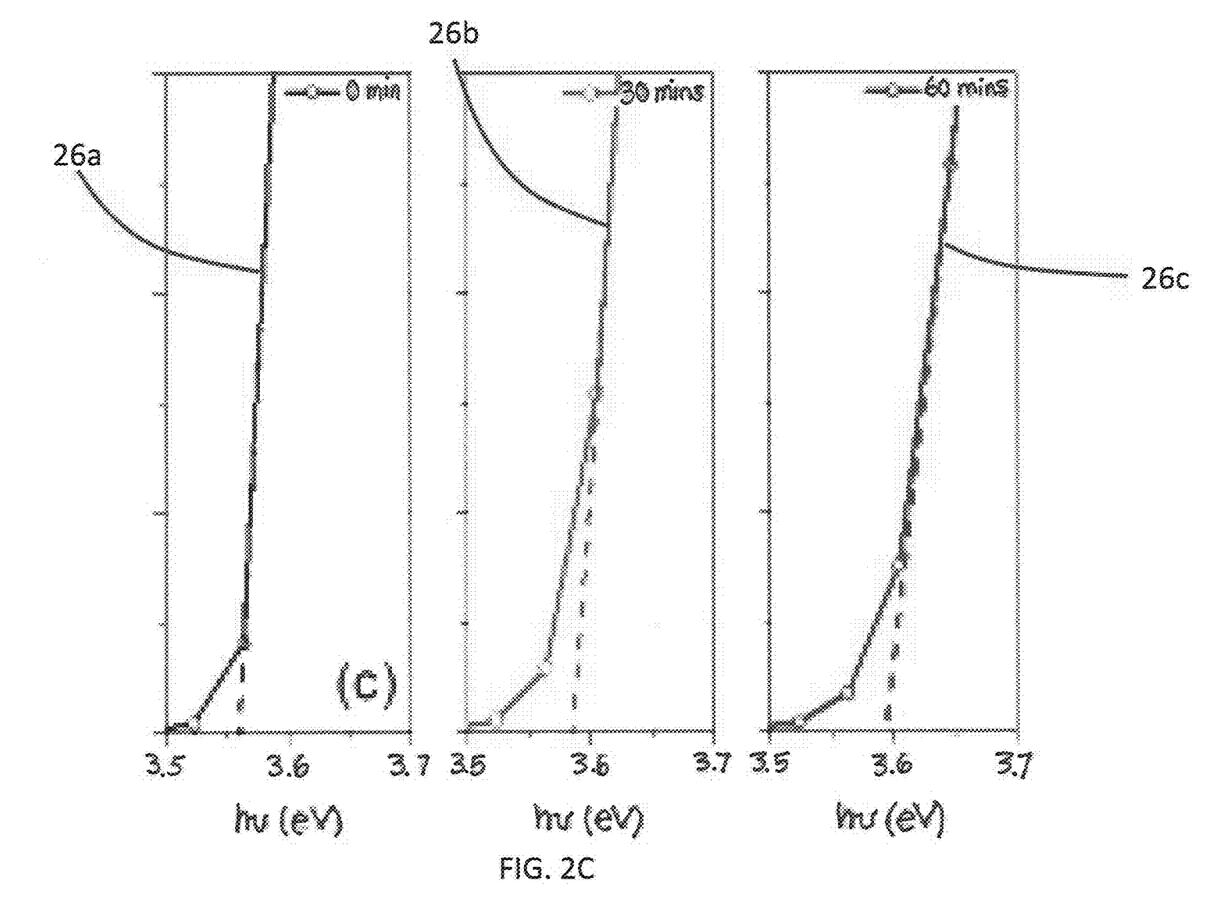
FIG. 2C shows the optical band gap energies of pure ligand with 0 minute, 60 minutes, and 120 minutes of UV exposure in accordance with some embodiments of the invention.
Figure 3A:
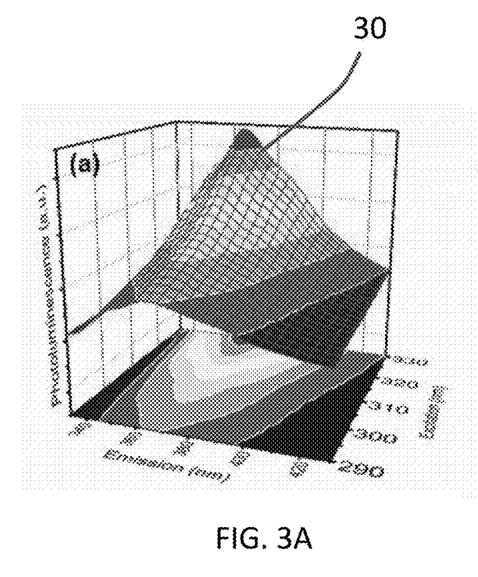
FIG. 3A shows photoluminescence spectra of diluted $H_2PDA$ in accordance with some embodiments of the invention.
Figure 3B:
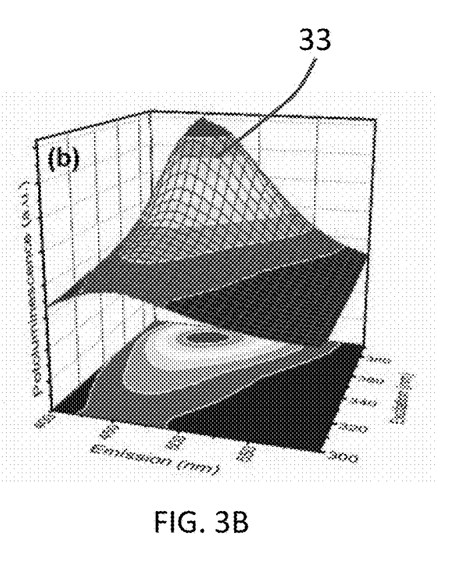
FIG. 3B shows photoluminescence spectra of ZrPDA before UV exposure in accordance with some embodiments of the invention.
Figure 3C:
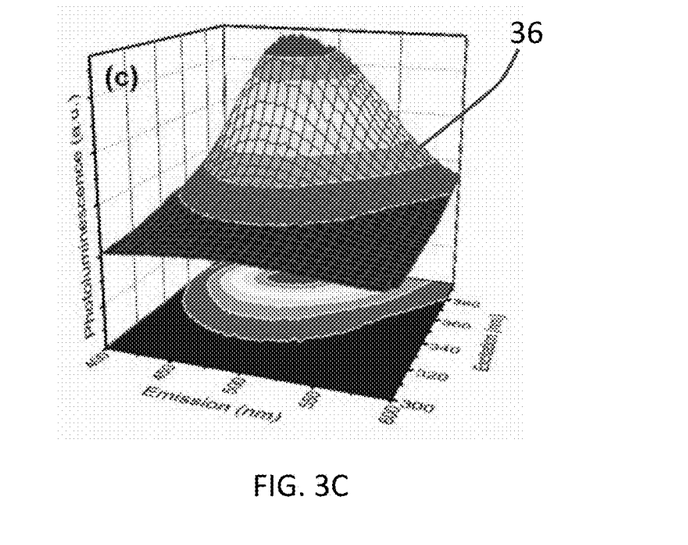
FIG. 3C shows photoluminescence spectra of ZrPDA with 120 minutes UV irradiation in accordance with some embodiments of the invention.

FIG. 2B shows the optical band gap energies of activated ZrPDA with 0 minute (shown as curve 24a), 60 minutes (shown as curve 24b), and 120 minutes of UV exposure (shown as curve 24c), in accordance with some embodiments of the invention. FIG. 2C shows the optical band gap energies of pure ligand with 0 minute (shown as curve 26a), 60 minutes (shown as curve 26b), and 120 minutes of UV exposure (shown as curve 26c), in accordance with some embodiments of the invention. FIG. 3A shows photoluminescence spectra 30 of diluted $H_2PDA$ in accordance with some embodiments of the invention. FIG. 3B shows photoluminescence spectra 33 of ZrPDA before UV exposure in accordance with some embodiments of the invention. FIG. 3C shows photoluminescence spectra 36 of ZrPDA with 120 minutes UV irradiation in accordance with some embodiments of the invention.

Figure 4A:
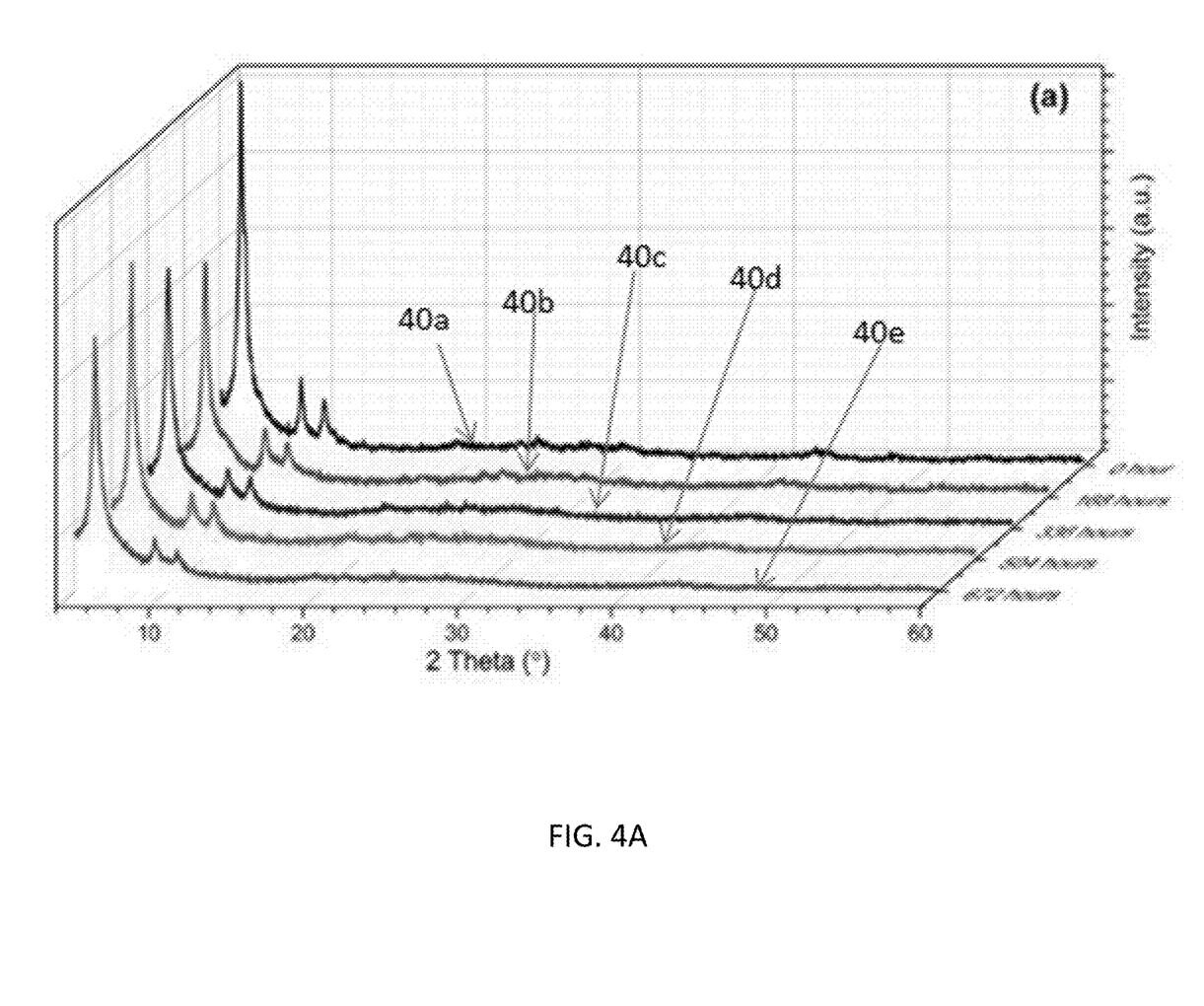
FIG. 4A shows powder XRD patterns of ZrPDA, as-synthesized, and soaked in water for 1 week, 2 weeks, and 3 weeks, and soaked in water for 4 weeks in accordance with some embodiments of the invention.
Figure 4B:
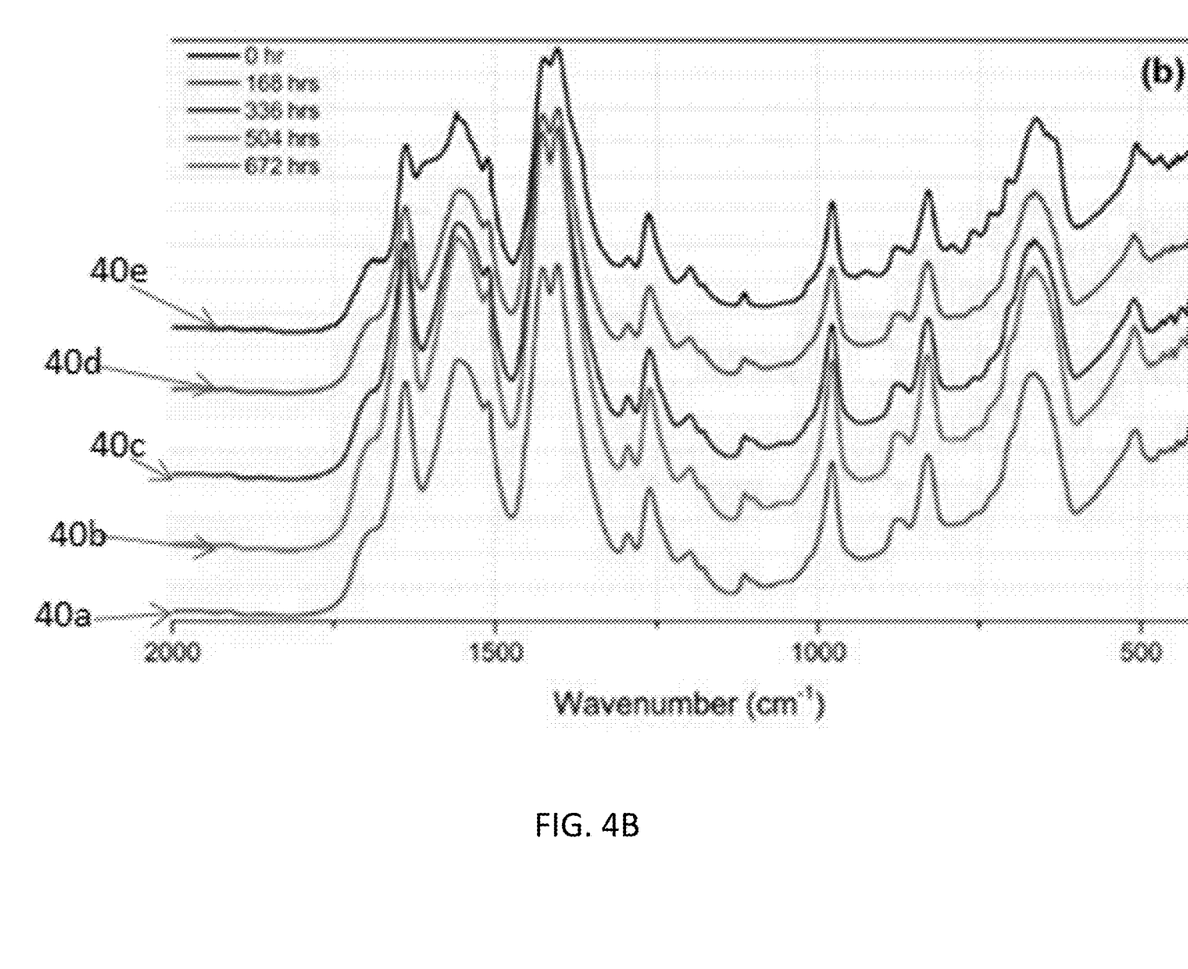
FIG. 4B shows FT-IR spectra from 2000 $cm^{-1}$ to 400 $cm^{-1}$ of ZrPDA with varying time of soaked under water in accordance with some embodiments of the invention.

The hydrostability of ZrPDA synthesized using the methods described herein was verified by immersion under water for 672 hours. The tested samples were analyzed by FT-IR spectrometer and high resolution X-ray diffractometer showing the stability of its crystal structure. For example, FIG. 4A shows powder XRD patterns of ZrPDA, as-synthesized (shown as curve 40a), and soaked in water for 1 week (shown as curve 40b), 2 weeks (shown as curve 40c), 3 weeks (shown as curve 40d), and soaked in water for 4 weeks (shown as curve 40e) in accordance with some embodiments of the invention. FIG. 4B shows FTIR spectra from 2000 to 400 cm$^{-1}$ of ZrPDA with varying time of soaked under water in accordance with some embodiments of the invention, with the soaking times as described for curves 40a, 40b, 40c, 40d, and 40e shown in FIG. 4A.

Figure 5:
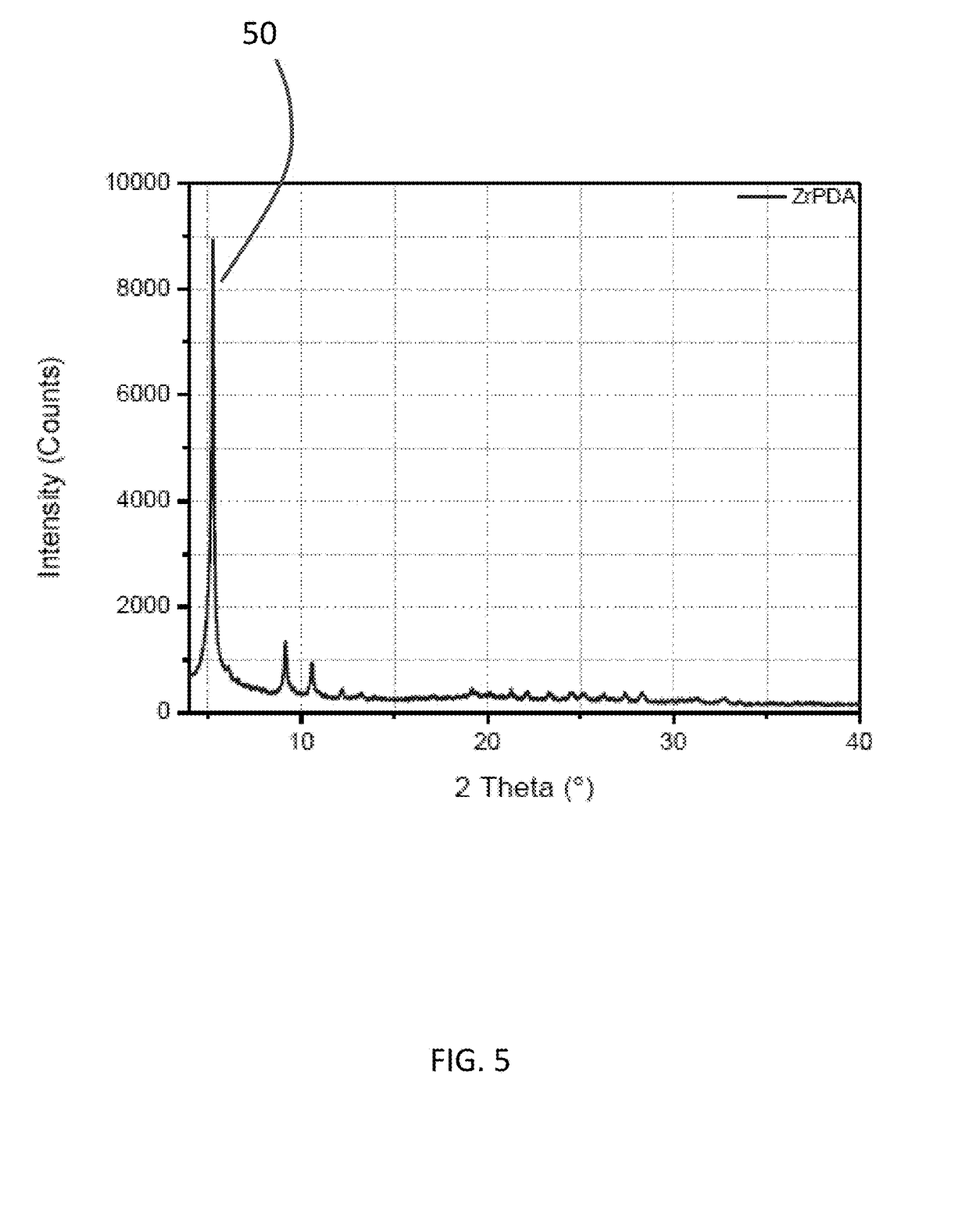
FIG. 5 shows a powder XRD pattern of the ZrPDA in accordance with some embodiments of the invention.
Figure 6:
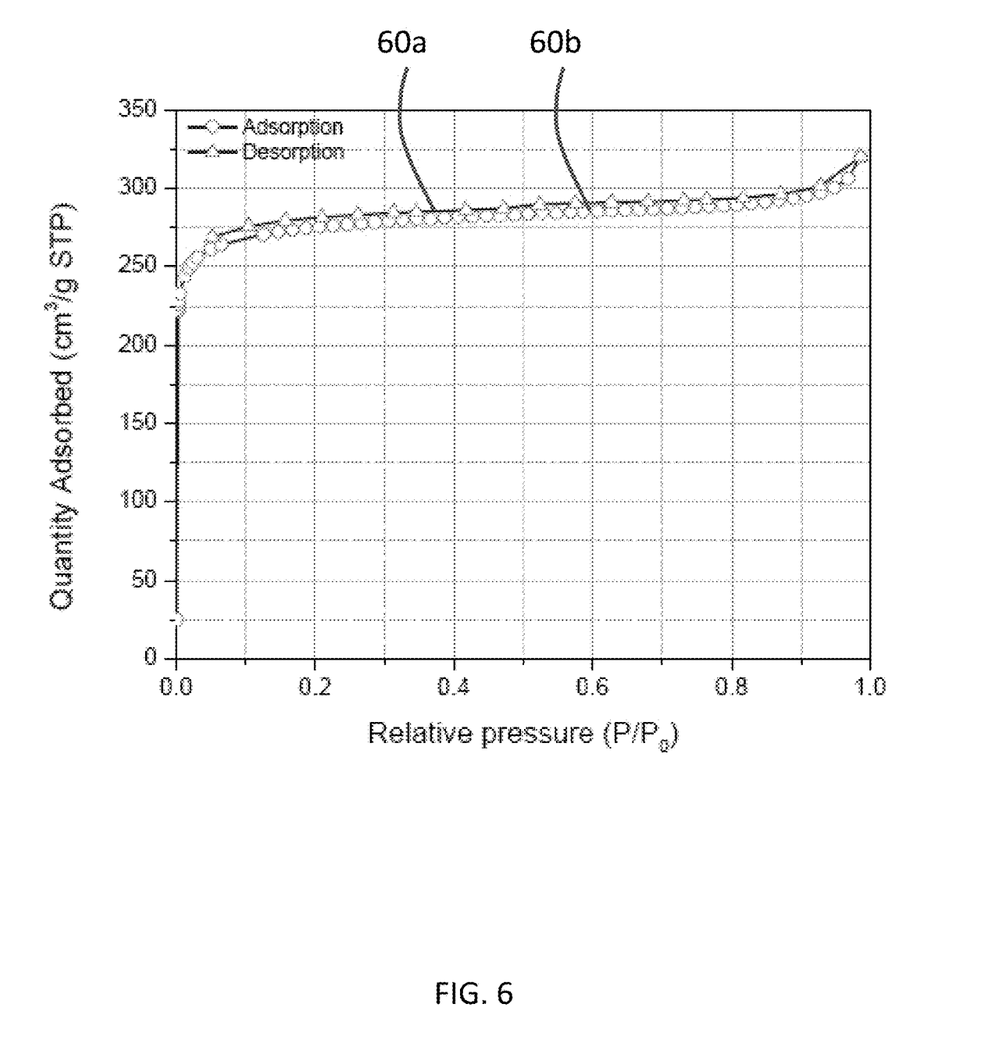
FIG. 6 shows an $N_2$ adsorption/desorption isotherm in accordance with some embodiments of the invention.
Figure 7:
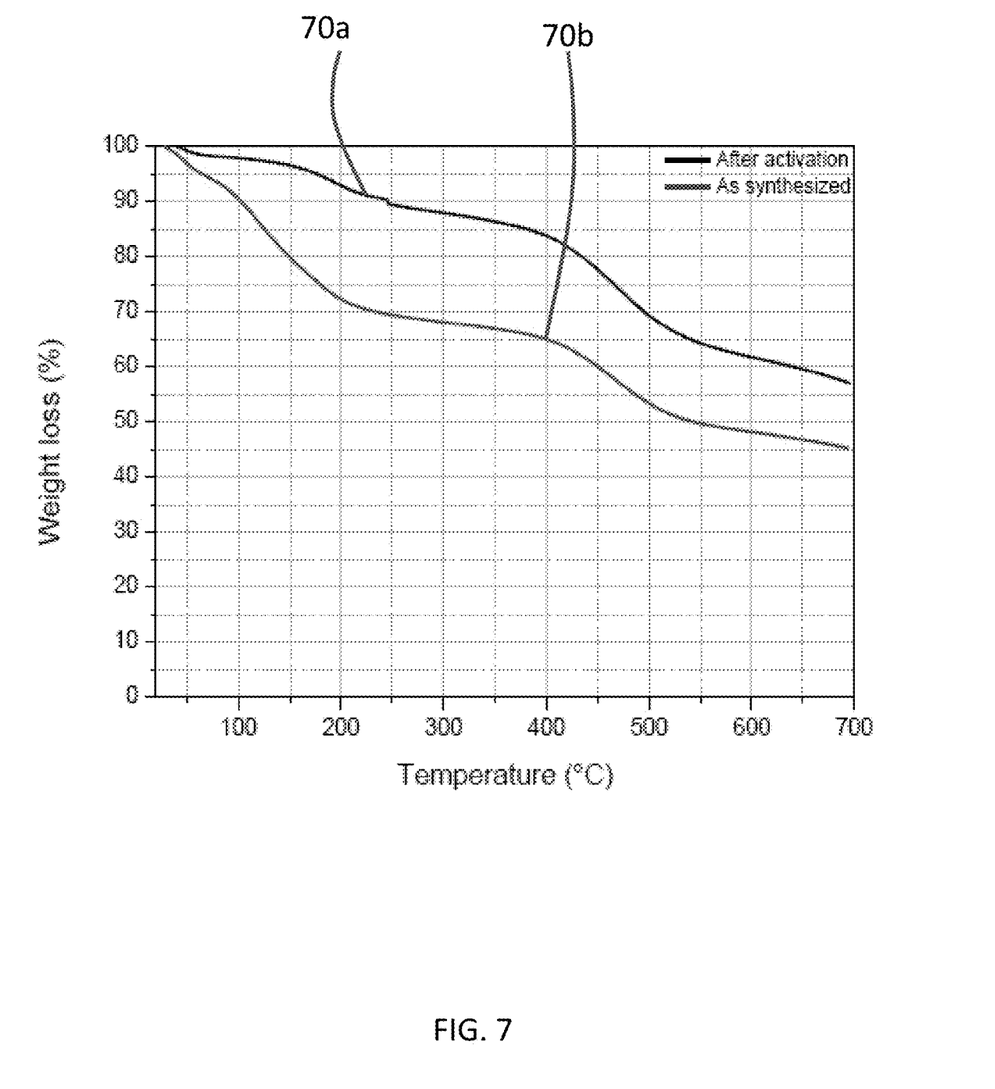
FIG. 7 illustrates thermogravimetric (TGA) curves of as-synthesized and activated ZrPDA samples accordance with some embodiments of the invention.

FIG. 5 shows a powder XRD pattern 50 of the ZrPDA in accordance with some embodiments of the invention. FIG. 6 shows an $N_2$ adsorption isotherm (curve 60a) and a an $N_2$ desorption isotherm (curve 60b) in accordance with some embodiments of the invention. FIG. 7 illustrates thermogravimetric (TGA) curves of as-synthesized (shown as curve 70b) and activated ZrPDA samples (shown as curve 70a) in accordance with some embodiments of the invention.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A metal-organic framework material preparation method comprising:
   1) in a first step, forming a first solution by dissolving $ZrOCl_2.8H_2O$ in dimethylformamide (DMF) and formic acid;
   2) in a second step, mixing and dissolving 1,4-phenylenediacrylic acid in a second solution of dimethylformamide (DMF) and trimethylamine;
   3) in a third step, at least partially mixing the first and second solutions to form a mixture; and
   4) in a fourth step, sealing the mixture in an autoclave and heating the mixture above ambient for a specified period of time to prepare ZrPDA metal-organic framework, the ZrPDA metal-organic framework being characterized by main peaks observed using X-ray powder diffraction (Cu Kα radiation) comprising the following 2θ angles: 5.3, 9.2, and 10.6.

2. The method of claim 1, wherein the second step occurs after completion of the first step.

3. The method of claim 1, wherein the second step is performed at least partially concurrently with the first step.

4. The method of claim 1, wherein during the fourth step, the mixture is heated to a temperature between ambient temperature and 200° C.

5. The method of claim 1, wherein during the fourth step, the mixture is heated to about 120° C.

6. The method of claim 1, wherein the specified period of time is between about 24 hours and 1 week.

7. The method of claim 1, wherein the specified period of time is about 24 hours.

8. The method of claim 1, further comprising a fifth step, wherein the ZrPDA metal-organic framework is washed with dimethylformamide (DMF).

9. The method of claim 8, wherein the ZrPDA metal-organic framework is washed with dimethylformamide (DMF) at least twice.

10. The method of claim 8, wherein the ZrPDA metal-organic framework is washed with dimethylformamide (DMF) three times per day for three days.

11. The method of claim 1, further comprising a sixth step, wherein the ZrPDA metal-organic framework is soaked in acetone and solvent exchanged for a specified exchange period.

12. The method of claim 11, wherein the solvent exchange occurs at least twice.

13. The method of claim 11, wherein the exchange period is three days, and the acetone is changed three times per day.

14. The method of claim 1, wherein the ZrPDA metal-organic framework is heated to about 100° C. in vacuum oven.

15. A method of preparing a phototuned metal-organic framework comprising:
   1) in a first step, forming a first solution by dissolving $ZrOCl_2.8H_2O$ in dimethylformamide (DMF) and formic acid;
   2) in a second step, mixing and dissolving 1,4-phenylenediacrylic acid in a second solution of dimethylformamide (DMF) and trimethylamine;
   3) in a third step, at least partially mixing the first and second solutions to form a mixture;
   4) in a fourth step, sealing the mixture in an autoclave and heating the mixture to above ambient temperature for a specified period of time to prepare ZrPDA metal-organic framework, the ZrPDA metal-organic framework being characterized by main peaks observed using X-ray powder diffraction (Cu Kα radiation) comprising the following 2θ angles: 5.3, 9.2, and 10.6; and
   5). in a fifth step, extracting the ZrPDA metal-organic framework and at least partially reacting to a specified degree at least some of ZrPDA metal-organic framework through [2+2] cycloaddition reactions, wherein the specified degree is tunable based at least in part on at least one of the intensity of UV radiation, the exposure time, and the UV wavelength.

16. The method of claim 15, wherein the specified time is between 24 hours and 1 week.

17. The method of claim 15, wherein in the fourth step, the mixture is heated to between 50° C. and 200° C.

18. The method of claim 15, wherein the UV wavelength is about 302 nm.

19. The method of claim 15, wherein the exposure time is greater than zero and less than 60 minutes.

20. The method of claim 15, wherein the exposure time is between about 60 minutes and 2 hours.

* * * * *